United States Patent [19]

Chopra et al.

[11] Patent Number: 5,028,432
[45] Date of Patent: Jul. 2, 1991

[54] PHARMACEUTICAL CAPSULES CONTAINING PANETIDINE

[75] Inventors: Sham K. Chopra, Bramalea; Tribhovan T. Makadia, Mississauga, both of Canada

[73] Assignee: Glaxo Canada, Inc., Canada

[21] Appl. No.: 482,903

[22] Filed: Feb. 22, 1990

[30] Foreign Application Priority Data

Feb. 23, 1989 [GB] United Kingdom ............... 8904182

[51] Int. Cl.$^5$ ............................................. A61K 9/48
[52] U.S. Cl. .................................. 414/451; 414/456; 414/484
[58] Field of Search .......................... 424/451, 456

[56] References Cited

U.S. PATENT DOCUMENTS

| | | | |
|---|---|---|---|
| 4,128,658 | 12/1978 | Price et al. | 514/471 |
| 4,521,431 | 6/1985 | Crookes | 514/471 |
| 4,610,990 | 9/1986 | Esanu | 514/302 |

FOREIGN PATENT DOCUMENTS

| | | |
|---|---|---|
| 2753526 | 8/1978 | Fed. Rep. of Germany . |
| 58-174308 | 8/1989 | Japan . |
| 2218333 | 11/1989 | United Kingdom . |
| 2222772 | 3/1990 | United Kingdom . |
| 050577 | 11/1990 | United Kingdom . |

OTHER PUBLICATIONS

Lachman et al., "The Nature of the Capsule Content", The Theory and Practice of Industrial Pharmacy, (2nd Edition), (1976), pp. 408-413.
The Pharmaceutical Codes (11th Edition) The Pharmaceutical Press, London, (1979) pp. 133-134.

*Primary Examiner*—Thurman Page
*Assistant Examiner*—Leon R. Horne
*Attorney, Agent, or Firm*—Bacon & Thomas

[57] ABSTRACT

The invention relates to a pharmaceutical composition in the form of a gelatin capsules consisting of a filling containing as active ingredient ranitidine or a physiologically acceptable salt thereof surrounded by a gelatin shell. The filling is formulated based on a non-aqueous matrix consisting of at least one fatty acid glyceride and/or mineral oil or paraffin. Preferably the matrix contains at least one surfactant. The matrix is essentially hydrophobic in character but is also sufficiently hydrophilic to permit dispersion and dissolution of the capsule filling in the gastrointenstinal tract.

16 Claims, No Drawings

PHARMACEUTICAL CAPSULES CONTAINING PANETIDINE

The present invention relates to a pharmaceutical composition containing as active ingredient the histamine $H_2$-antagonist ranitidine, more particularly a composition for oral administration.

Ranitidine, N-[2-[[[5-(dimethylamino)methyl-2-furanyl]methyl]thio]ethyl]-N'-methyl-2-nitro-1,1-ethenediamine, and its physiologically acceptable salts are described and claimed in British Patent Specification No. 1565966, and a particular crystalline form of ranitidine hydrochloride is described and claimed in British Patent Specification No. 2084580B. In both of these specifications there is reference to a variety of formulations including preparations for oral, topical, parenteral or rectal administration. Particular types of aqueous formulation for oral use are further described in British Patent Specifications Nos. 2142820A and 2198352A.

Oral administration constitutes a preferred route for administering ranitidine, and tablets and capsules represent particular types of formulation for oral use. Capsules conventionally possess an outer shell of which the prime ingredient is gelatin, and in general such capsules may be presented as either hard or soft gelatin capsules.

Gelatin capsules provide a useful and advantageous means of formulating drug substances and, in particular, permit incorporation of the active ingredient in the form of a semi-solid, liquid or paste. The outer shells of gelatin capsules contain gelatin and water as basic ingredients. However, the presence of a certain amount of moisture in the capsule shell constitutes a disadvantage when seeking to formulate drugs such as ranitidine and certain of its physiologically acceptable salts, more particularly ranitidine hydrochloride, which are soluble in water to an appreciable extent.

A non-aqueous fill matrix has now been found which enables ranitidine to be satisfactorily formulated as gelatin capsules. The fill matrix is essentially hydrophobic in character, but is also sufficiently hydrophilic to permit dispersion and dissolution of the capsule filling in the gastrointestinal tract, so that the drug substance is satisfactorily absorbed in the body. The resulting gelatin capsules constitute a stable formulation, and the relatively hydrophobic, non-aqueous nature of the fill matrix minimises diffusion of the ranitidine into the capsule shell and migration of water from the shell into the matrix.

Thus according to one aspect the present invention provides a pharmaceutical composition in the form of gelatin capsules consisting of a filling containing ranitidine or a physiologically acceptable salt thereof as the active ingredient surrounded by a gelatin shell. The composition is characterised in that the filling is based on a non-aqueous matrix consisting of at least one fatty acid glyceride and/or mineral oil or paraffin.

The composition preferably contains at least one surfactant. This may be a conventional surfactant such as a sorbitan derivative (e.g. polysorbate 80) or, more particularly, lecithin. Alternatively, and more preferably, at least one of the fatty acid glycerides may possess surfactant properties.

According to a preferred embodiment of the invention the matrix consists of a mixture of fatty acid glycerides and/or mineral oils, in which at least one component of the mixture (e.g. at least one of the fatty acid glycerides) possesses surfactant properties.

The capsules according to the invention may be hard or, more preferably, soft gelatin capsules, and chewable soft gelatin capsules are also included within the scope of the invention.

The non-aqueous fill matrix constitutes a further aspect of the invention.

In a particularly preferred embodiment of the invention, the fill matrix contains two oily excipients, the first of which is a mixture of glycerides (e.g. triglycerides) of medium chain (e.g. $C_8$–$C_{10}$) fatty acids (e.g. fractionated $C_8$–$C_{10}$ coconut fatty acids). This component constitutes a neutral oily excipient, and a particularly suitable neutral oil of this type is that known under the Trade Mark Miglyol 812 (available from Dynamit Nobel Co.).

The second oily excipient in the particularly preferred fill matrix is a mixture of glycerides (e.g. mono-, di- and/or tri glycerides) of long chain (e.g. $C_{12}$–$C_{18}$) fatty acids. This component is preferably selected from the range of products known under the Trade Mark Gelucire (available from Gattefosse Corporation). In general, such mixtures have surfactant properties and, in particular, Gelucires are available with varying physical characteristics, and are identified by their melting point/HLB value, where the HLB (Hydrophile-Lipophile Balance) value is a measure of the hydrophobic or hydrophilic nature of the substance. The lower the number, the more hydrophobic the material, and Gelucires 33/01, 35/10 and 37/02 represent preferred products for use according to the present invention, of which Gelucire 33/01 is particularly preferred. In addition to its hydrophobic properties, Gelucire 33/01 is non-polar in nature and possesses surfactant properties.

Further examples of non-aqueous oily excipients that may be used in the fill matrix of the invention include mineral oils such as liquid paraffin, solid paraffins such as petrolatum, and the triglyceride range of products known under the Trade Mark Wecobee.

In addition to the non-aqueous excipients and where appropriate an additional surfactant, the capsule filling may if desired contain additional ingredients such as preservatives, flavouring and/or sweetening agents.

In addition to being incorporated into gelatin capsules, the non-aqueous matrix containing ranitidine or a physiologically acceptable salt thereof may be formulated as a non-aqueous composition, for example an oil-based suspension for oral administration as a liquid, using a suitable pharmaceutically acceptable non-aqueous vehicle such as coconut oil. Such non-aqueous compositions are also included within the scope of the invention.

Ranitidine may be employed in the composition according to the invention either as the free base or, more preferably, in the form of a physiologically acceptable salt. Such salts include salts of inorganic or organic acids such as hydrochloride, hydrobromide, sulphate, acetate, maleate, succinate, fumarate and ascorbate salts. A particularly preferred salt for use according to the invention is the hydrochloride.

The amount of ranitidine, preferably in the form a physiologically acceptable salt, in the composition of the invention is preferably in the range of 50–800 mg, more preferably 150–600 mg, per dosage unit, expressed as the weight of free base. The amount of ranitidine, preferably in the form of a physiologically acceptable salt, may for example be in the range of 50–500 mg, and 150–300 mg per dosage unit (expressed as the weight of free base) represents a particularly preferred amount.

The ranitidine content of the filling (in the form of either free base or a physiologically acceptable salt) may be, for example, in the range of 30% to 70% on a weight to weight (w/w) basis, more preferably 45% to 55% (w/w).

Where a surfactant is added to the matrix, this may constitute for example 0.1% to 8% (w/w) of the fatty acid glyceride and/or mineral oil or paraffin mixture.

In a preferred embodiment of the invention, the fill matrix contains two oily excipients, the first of which (e.g. Miglyol 812) may constitute for example 20% to 60% (w/w), more preferably 30% to 40% (w/w), of the filling. The second oily excipient (e.g. Gelucire 33/01), possessing surfactant properties, may constitute for example 5% to 35% (w/w), more preferably 10% to 25% (w/w) of the filling.

A preferred fill matrix according to the invention comprises ranitidine hydrochloride, Miglyol 812 and Gelucire 33/01.

The outer shells surrounding the filling are of the conventional type used in manufacturing gelatin capsules. Soft gelatin capsules, in addition to containing gelatin and water, also contain a plasticiser (e.g. glycerin and/or sorbitol). Additional ingredients such as colouring and opacifying agents may also be included.

The compositions according to the invention are intended for human or veterinary use. They may be administered, for example, 1 to 4 times daily, preferably once or twice. It will be appreciated that it may be necessary to make routine variations to the dosage depending on the age and weight of the patient, and the nature and severity of the condition being treated.

The composition of the invention may, if desired, be adapted to permit slow release of the ranitidine.

The compositions according to the invention may be prepared according to conventional techniques known in the pharmaceutical industry for the manufacture of gelatin capsules. Thus, for example, the fill matrix may be prepared by adding the ranitidine or ranitidine salt to a molten homogeneous mixture of the fatty acid glyceride(s) and/or mineral oil(s) or paraffin(s), and surfactant if required, followed by thorough mixing and milling. Additional ingredients such as preservatives, flavouring and/or sweetening agents may be included as appropriate. Preparation of the gelatin mass for the shells and the subsequent encapsulation may be achieved using standard techniques.

The following Examples illustrate soft gelatin capsules according to the invention, in which the active ingredient is ranitidine hydrochloride. Ranitidine free base or other physiologically acceptable salts thereof may be formulated in a similar manner.

EXAMPLE 1

|  | mg per capsule | |
|---|---|---|
|  | For 150 mg capsule | For 300 mg capsule |
| Ranitidine hydrochloride | 168.0* | 336.0** |
| Miglyol 812 | 125.0 | 250.0 |
| Gelucire 33/01 | 57.0 | 114.0 |
| Fill weight per capsule | 350.0 mg | 700.0 mg |

*Equivalent to 150 mg ranitidine free base
**Equivalent to 300 mg ranitidine free base The required quantities of Miglyol 812 and Gelucire 33/01 were added to a heated vessel, and the contents stirred until the Gelucire had melted and the mixture was clear. The mixture was then transferred to a mixing vessel and the ranitidine hydrochloride was added. A high speed mixer was lowered into the vessel and the contents mixed for about 15 minutes. The resulting mixture was milled using a suitable milling apparatus to ensure that the powder was adequately wetted and that no aggregates remained.

The filling was subsequently encapsulated with an appropriate gelatin mass to give soft gelatin capsules containing 150 mg or 300 mg ranitidine per capsule as required.

If desired the filling prepared as described above may be encapsulated in hard gelatin capsule shells.

EXAMPLE 2

|  | mg per capsule |
|---|---|
| Ranitidine hydrochloride | 672.0* |
| Miglyol 812 | 435.0 |
| Lecithin | 21.0 |
| Fill weight per capsule | 1128.0 mg |

*Equivalent to 600 mg ranitidine free base.

The Miglyol 812 and lecithin were mixed to give a homogeneous mixture. Whilst this was being stirred, the ranitidine hydrochloride was added slowly. The resulting homogeneous mixture was milled using a suitable apparatus, and subsequently encapsulated with an appropriate gelatin mass to give soft gelatin capsules containing 600 mg ranitidine per capsule.

If desired the filling prepared as described above may be encapsulated in hard gelatin capsule shells.

We claim:

1. A pharmaceutical composition in the form of gelatin capsules comprising a filling containing as active ingredient ranitidine or a physiologically acceptable salt thereof surrounded by a gelatin shell, said filling being based on a non-aqueous matrix consisting essentially of at least one fatty acid glyceride and/or mineral oil or paraffin.

2. A pharmaceutical composition according to claim 1 in which said matrix contains at least one surfactant.

3. A pharmaceutical composition according to claim 2 in which said matrix consisting essentially of a mixture of fatty acid glycerides and/or mineral oils or paraffins in which at least one component of the mixture possesses surfactant properties.

4. A pharmaceutical composition according to claim 2 in which said surfactant is lecithin.

5. A pharmaceutical composition according to claim 1 in which said gelatin shell is a soft gelatin shell.

6. A pharmaceutical composition according to claim 1 in which said filling contains 30 to 70% (w/w) ranitidine in the form of either free base or physiologically acceptable salt.

7. A pharmaceutical composition according to claim 1 containing ranitidine in the form of ranitidine hydrochloride.

8. A pharmaceutical composition in the form of gelatin capsules consisting essentially of a filling containing as active ingredient ranitidine or a physiologically acceptable salt thereof surrounded by a gelatin shell, said filling being based on a non-aqueous matrix comprising a first oily excipient which is a mixture of glycerides of medium chain fatty acids and a second oily excipient which is a mixture of glycerides of long chain fatty acids.

9. A pharmaceutical composition according to claim 8 in which said first oily excipient is a mixture of triglycerides of $C_8$–$C_{10}$ fatty acids and said second oily excipient is a mixture of mono-, di-, and/or triglycerides of $C_{12}$–$C_{18}$ fatty acids.

10. A pharmaceutical composition according to claim 9 in which said first oily excipient comprises 20% to 60% (w/w) of said filling and said second oily excipient comprises 5 to 35% (w/w) of said filling.

11. A pharmaceutical composition according to claim 8 in which said gelatin shell is a soft gelatin shell.

12. A pharmaceutical composition according to claim 8 in which said filling contains 30 to 70% (w/w) ranitidine in the form of either free base or physiologically acceptable salt.

13. A pharmaceutical composition according to claim 8 containing ranitidine in the form of ranitidine hydrochloride.

14. A pharmaceutical composition according to claim 8 containing ranitidine hydrochloride as active ingredient in which said ranitidine hydrochloride comprises 45% to 55% (w/w) of said filling and said filling is based on a non-aqueous matrix consisting essentially of a first oily excipient which is a mixture of triglycerides of $C_8$–$C_{10}$ fatty acids and comprises 30% to 40% (w/w) of said filling, and a second oily excipient which is a mixture of mono-, di- and/or triglycerides of $C_{12}$–$C_{18}$ fatty acids and comprises 10% to 25% (w/w) of said filling.

15. A composition suitable for use as a filling for gelatin capsules comprising ranitidine or a physiologically acceptable salt thereof and a non-aqueous matrix consisting essentially of at least one fatty acid glyceride and/or mineral oil or paraffin.

16. A non-aqueous pharmaceutical composition comprising ranitidine or a physiologically acceptable salt thereof and a non-aqueous matrix consisting essentially of at least one fatty acid glyceride and/or mineral oil or paraffin together with a pharmaceutically acceptable non-aqueous vehicle.

* * * * *

UNITED STATES PATENT AND TRADEMARK OFFICE
CERTIFICATE OF CORRECTION

PATENT NO. : 5,028,432
DATED : July 2, 1991
INVENTOR(S) : Sham K. CHOPRA et al

It is certified that error appears in the above-identified patent and that said Letters Patent is hereby corrected as shown below:

ON THE TITLE PAGE, ITEM [54], AND IN COLUMN 1, LINE 2,
IN THE TITLE:

Please delete "PANETIDINE" and insert --RANITIDINE--.

COLUMN 4, LINE 47:

Claim 3, line 2, delete "consisting" and insert --consists--.

Signed and Sealed this

Second Day of February, 1993

*Attest:*

STEPHEN G. KUNIN

*Attesting Officer*   Acting Commissioner of Patents and Trademarks

UNITED STATES PATENT AND TRADEMARK OFFICE
CERTIFICATE OF CORRECTION

PATENT NO. : 5,028,432

DATED : July 2, 1991

INVENTOR(S) : Sham K. CHOPRA et al.

It is certified that error appears in the above-identified patent and that said Letters Patent is hereby corrected as shown below:

IN THE CLAIMS:
    Column 4,

Claim 8, line 2, change "consisting essentially of" to --comprising--; and
line 5, change "comprising" to --consisting essentially of--.

Signed and Sealed this

Fifth Day of December, 1995

Attest:

BRUCE LEHMAN

Attesting Officer    Commissioner of Patents and Trademarks